(12) United States Patent
Kangas et al.

(10) Patent No.: US 7,756,646 B2
(45) Date of Patent: Jul. 13, 2010

(54) METHOD FOR PREDICTING PEPTIDE DETECTION IN MASS SPECTROMETRY

(75) Inventors: Lars Kangas, West Richland, WA (US); Richard D. Smith, Richland, WA (US); Konstantinos Petritis, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 1099 days.

(21) Appl. No.: 11/394,839

(22) Filed: Mar. 31, 2006

(65) Prior Publication Data

US 2007/0233394 A1 Oct. 4, 2007

(51) Int. Cl.
*G01N 31/00* (2006.01)
*G01N 33/48* (2006.01)

(52) U.S. Cl. .............................. 702/22; 702/19; 702/23; 530/417

(58) Field of Classification Search ........................ None
See application file for complete search history.

(56) References Cited

U.S. PATENT DOCUMENTS 6,675,104 B2 * 1/2004 Paulse et al. .................. 702/22
7,136,759 B2 * 11/2006 Kangas et al. ................. 702/19

OTHER PUBLICATIONS

MacCoss et al. Anal. Chem. 2002, 74, p. 5593-5599.*
Cannon et al. J Proteome Res. Sep. 2005, 4(5), p. 1687-1698.*
Keller et al. Anal. Chem. 2002, 74, 5383-5392.*

* cited by examiner

*Primary Examiner*—Michael Borin
(74) *Attorney, Agent, or Firm*—Douglas E. McKinley, Jr.

(57) ABSTRACT

A method of predicting whether a peptide present in a biological sample will be detected by analysis with a mass spectrometer. The method uses at least one mass spectrometer to perform repeated analysis of a sample containing peptides from proteins with known amino acids. The method then generates a data set of peptides identified as contained within the sample by the repeated analysis. The method then calculates the probability that a specific peptide in the data set was detected in the repeated analysis. The method then creates a plurality of vectors, where each vector has a plurality of dimensions, and each dimension represents a property of one or more of the amino acids present in each peptide and adjacent peptides in the data set. Using these vectors, the method then generates an algorithm from the plurality of vectors and the calculated probabilities that specific peptides in the data set were detected in the repeated analysis. The algorithm is thus capable of calculating the probability that a hypothetical peptide represented as a vector will be detected by a mass spectrometry based proteomic platform, given that the peptide is present in a sample introduced into a mass spectrometer.

6 Claims, 4 Drawing Sheets

US 7,756,646 B2

METHOD FOR PREDICTING PEPTIDE DETECTION IN MASS SPECTROMETRY

The invention was made with Government support under Contract DE-AC0676RLO 1830, awarded by the U.S. Department of Energy. The Government has certain rights in the invention.

TECHNICAL FIELD

This invention relates to methods of utilizing mass spectrometers for analyzing biological samples. More specifically, the present invention is a method of predicting whether a peptide present in a biological sample will be detected by analysis with a mass spectrometer.

BACKGROUND OF THE INVENTION

A growing numbers of essentially complete genome sequences now available allows global identification of proteins responding to specific physiological conditions to enable understanding of cellular pathways and networks. A review of this research is published in the publications which follow (these and all other papers, references, patents, or other published materials cited or referenced herein are hereby incorporated herein in their entirety by this reference):

Wilkins, M. R., Williams, K. L., Appel, R. D., Hochstrasser, D. F. Eds., *"Proteome Research: New Frontiers in Functional Genomics,"* Springer, Berlin, Germany, 1997.

Devine, K. M., Wolfe, K. *Trends Genet* 1995, 11, 429-431.

Uddhav, K., Ketan, S., *Mol. Bio. Rep.* 1998, 25, 27-43.

*Genome Sequence of the Nematode C. elegans: A Platform for Investigating Biology*, Science, 1998, 282, 2012-2018. Adams, M. D., Bioassays 1996, 18, 261-262. Anderson, L., Seilhammer, J., *Electrophoresis* 1997, 18, 533-537.

Resources on the internet which provide access to these sequences include http://www.ebi.ac.uk/research/cgg/genomes.html and http://www.ncbi.nlm.nih.gov/Entrez/Genome/main_genomes.html Proteome analyses using either two dimensions (as shown in Washburn, M. P.; Wolters, D.; Yates, J. R. *Nat. Biotechnol.* 2001, 19, 242-247) or one dimension (as shown in Shen, Y.; Zhang, R.; Moore, R. J.; Kim, J. K.; Metz, T. O.; Hixson, K. K.; Zhao, R.; Livesay, E. A.; Udseth, H. R.; Smith, R. D. *Anal. Chem.* 2005, 77, 3090-3100) of liquid chromatography (LC) with tandem mass spectrometry (MS/MS) has become an important tool for protein identification due to its ability to rapidly identify complex mixtures of proteins with high sensitivity and limited bias. The dominant "bottom-up" approach described in these references allows for the identification of enzymatically produced (e.g., tryptic) peptides, and inference of the parent protein, due to the sequence related nature of peptide ion fragmentation, and the use of automated database searches (i.e., comparison of MS/MS spectra with theoretical spectra predicted from peptide sequence information as described in Eng, J. K.; McCormack, A. L.; Yates, J. R. *Am. Soc. Mass Spectrm*, 1994, 5, 976-989.)

The challenges associated with accurate identification in "bottom-up" proteomics are significant due to the complexity of the peptide mixtures. For example, a genome coding for ~5,000 proteins can potentially produce >250,000 tryptic peptides.

At the same time, advances in instrumentation allow very large numbers of MS/MS spectra to be generated rapidly. While large amounts of data can easily be produced, the data suffers from variations in spectrum quality, protein abundances, sequence specific differences in dissociation pathways, the contributions of modified peptides, contaminates, and limitations on mass measurement accuracy. The reasons for these variations are described in the following publications:

Huang, Y.; Triscari, J. M.; Tseng, G. C.; Pasa-Tolic, L.; Lipton, M. S.; Smith, R. D.; Wysocki, V. H. *Anal. Chem.* 2005, 77, 5800-5813.

Peng, J.; Elias, J. E.; Thoreen, C. C.; Licklider, L. J.; Gygi, S. P. *J. Proteome Res.* 2003, 2, 43-50.

Keller, A.; Nesvizhskii, A. I.; Kolker, E.; Aebersold, R. *Anal. Chem.* 2002, 74, 5383-5392.

Strittmatter, E. F.; Kangas, L. J.; Petritis, K.; Mottaz, H. M.; Anderson, G. A.; Shen, Y.; Jacobs, J. M.; Camp, D. G.; Smith, R. D. *J. Proteome Res.* 2004, 3, 760-769.

The forgoing problems can result in significant levels of false positive identifications. In Peng, J.; Elias, J. E.; Thoreen, C. C.; Licklider, L. J.; Gygi, S. P. *J. Proteome Res.* 2003, 2, 43-50 and Shen, Y., Kim, J.; Strittmatter, E. F.; Jacobs, J. M.; Capm, D. G.; Fang, R.; Tolic, N.; Moore, R. J.; Smith, R. D. *PROTEOMICS*, 2005, 5, 4034-404, reverse-database and cross-database methods are purposed for evaluation of peptide false identification rates. However, these methods fail to generally define clear boundaries between true/false positive/negative identifications, and the rates of false positive identifications increase approximately linearly with the number of possible peptides in the theoretical database for the system being studied (i.e. approximately with the size of the proteome). Furthermore, these methods deal with the peptides as population and do not provide any information for the individual peptides. As a result, increasing the database matching score criteria decreases the rate of identifying false positives, but simultaneously increases the probability of missed peptide identifications (i.e., a higher false negative rate).

Recently, in Craig, R.; Cortens, J. P.; Beavis, R. C., "The use of proteotypic peptide libraries for protein identification" *Rapid Communications in Mass Spectrometry* 2005, 19, (13), 1844-1850 and Kuster, B.; Schirle, M.; Mallick, P.; Aebersold, R., "Scoring proteomes with proteotypic peptide probes" *Nature Reviews Molecular Cell Biology* 2005, 6, (7), 577-583 the term proteotypic was coined for peptides in a protein sequence that is more likely to be confidently observed by a specific MS based proteomic method. Knowledge of the proteotypic peptides is very important in proteomics as it can increase the through-put and allow quantitative results to be obtained. It has even been suggested that accurate knowledge of the proteotypic peptides could lead on a paradigm shift of how proteomics is performed. Indeed, Beavis and co-workers showed that the knowledge of the proteotypic peptides can decrease the identification calculations by as much as 20-fold. Furthermore, Aebersold and co-workers indicated that once the proteotypic peptides of an organism are known, it is possible to synthesize heavy isotopes of these peptides, spike them in the sample of interest and achieve absolute quantitative data. In Le Bihan, T.; Robinson, M. D.; Stewart, I. I.; Figeys, D., "Definition and characterization of a "trypsinosome" from specific peptide characteristics by Nano-HPLC-MS/MS and in silico analysis of complex protein mixtures" *J. Proteome Res.* 2004, 3, 1138-1148, Le Bihan et al. showed that knowledge of the proteotypic peptides can help the identification of the low abundant proteins through inclusion lists that target the parent ions of these peptides.

The assumption that every peptide has an equal likelihood of detection and identification by LC-MS is not supported by the experience of scientists engaged in proteomic research. Indeed, even in cases where only one pure standard protein is digested by trypsin and analyzed by LC-MS, protein coverage of 100% is rarely observed. Differences in which peptides are observed, and the failure to observe certain peptides in any particular experiment, are generally the result of the specifics of the proteomic platform used for a particular experiment.

As used herein, a "proteomic platform" refers to the combination of the steps commonly performed to identify peptides in proteomic research; sample preparation, sample simplification, mass spectrometry, and the application of bioinformatic tools to the resulting data. As will be recognized by those having skill in the art, significant variations in the specifics of each of these steps exist, and these variations will have a significant impact on which peptides are observed.

Differences in sample preparation, such as the protein extraction methodology and/or the denaturing agents used for digestion, will lead to different peptides being observed. For example, while trypsin is perhaps the most commonly used enzyme in sample preparation, it is just one of the enzymes that may be used for the digestion of the proteins. Different chemical or enzymatic denaturing agents will effect which peptides present in the sample are ultimately observed. Also, the nature of solid phase extraction used for cleanup purposes will also affect which peptides will be observed.

Sample simplification refers to the very commonly used pre-fractionation and/or separation techniques often used for protein/peptide simplification before analysis by MS. For example, it is common to separate peptides by reversed phase liquid chromatography (RPLC) before analysis by mass spectrometry. During this step, very hydrophilic peptides might not be retained on the column and will elute in the void volume while highly hydrophobic peptides can be bound irreversibly in the stationary phase. In both cases, these peptides will generally not be detected. Furthermore, it is also very common, especially in cases of very complex proteomes, to perform a peptide pre-fractionation by using strong cation exchange (SCX) before RPLC-MS. While this approach generally reveals more peptides overall, there are several classes of peptides that might bind irreversibly to the SCX and never make it to the RPLC-MS. These peptides could be otherwise detected by a simple RPLC-MS analysis if the pre-fractionation had not been used.

With respect to mass spectrometry, the reasons peptides are not identified include the inability of certain peptides to ionize into the gas phase in sufficient quantities to give a detectable signal and/or to give interpretable MS/MS spectra (in the case of MS/MS experiments). For example, it has been widely observed in proteomics that peptides from the same protein produce a range of detected intensities, with a fraction of the peptides from each protein falling below the detection limit. It should be understood that as the term is used herein, "mass spectrometry" includes all of the different ionization techniques used, included but not limited, ESI, MALDI, APCI, either alone or in combination, and the different fragmentation techniques used, including but not limited to CID, ETD, ECD either alone or in combination. Differences in both the ionization techniques and the fragmentation techniques will lead to differences in the observed peptides.

Finally, the same LC-MS/MS data analyzed by different parameters and by different informatics tools results in somewhat different peptide identifications even when normalized to the same rate of false positives. This is because of the difference in scoring schemes used by different tools to interpret mass spectra. For example, MS/MS peptide identification software such as SEQUEST, Spectrum Mill, Mascot, and X-Tandem give peptide identification overlap of only about 70% for the same LC-MS/MS analyses and same false positive rate. This means that for the same proteomic platforms (i.e. same biological sample, same sample preparation, same sample simplification technique, same ionization and same mass spectrometer analyzer) and only different data analysis software (i.e. as an example between SEQUEST and Mascot), there are going to be only about 700 identical peptides identified between the two software tools for every 1000 total peptides identified.

These and other difficulties associated with identifying peptides in proteomic platforms has resulted in the development of various techniques which attempt to predict if a peptide will be accurately identified. For example, in Le Bihan, T.; Robinson, M. D.; Stewart, I. I.; Figeys, D., "Definition and characterization of a "trypsinosome" from specific peptide characteristics by Nano-HPLC-MS/MS and in silico analysis of complex protein mixtures" J. Proteome Res. 2004, 3, 1138-1148 the authors describe a model that can predict if a peptide will be identified in a proteomic platform. This study used three peptide physiochemical properties: hydrophobicity, isoelectric point (pI) and the length of a peptide to generate the prediction. In Ethier, M.; Figeys, D., "Strategy to design improved proteomic experiments based on statistical analyses of the chemical properties of identified peptides" Journal of Proteome Research 2005, 4, (6), 2201-2206) the authors extended Le Bihan's algorithm by using different weights for the hydrophobicity, pI and length of the peptides. They further trained the weights with data from 13 different proteomic platforms and used clustering analysis to group the platforms into different groups. Finally, Kuster et al. (Kuster, B.; Schirle, M.; Mallick, P.; Aebersold, R., "Scoring proteomes with proteotypic peptide probes" Nature Reviews Molecular Cell Biology 2005, 6, (7), 577-583) mentioned a computational approach for the identification of proteotypic peptides based on 500 different peptide physicochemical properties.

Drawbacks and limitations associated with these and other methods create a need for improved methods and techniques for predicting whether peptides will be detected in mass spectrometric analysis that simultaneously decrease the rate of false positive identifications and decrease the rate of false negative identifications.

SUMMARY OF THE INVENTION

Accordingly, one object of this invention is to provide a method for identifying peptides in mass spectrometry based proteomic platforms, that when combined with additional information, can simultaneously decrease the rates of both false positive identifications and false negative identifications. Examples of additional information include, but are not limited to a) scores given by different software tools such as the Xcorr from the Sequest software, b) the difference between the theoretical and measured molecular weight of the peptide, c) the difference between the predicted and measured retention time of the peptide.

A second object of the present invention is to provide a method for predicting the probability that a peptide will be detected by a mass spectrometer, given that it is present in a sample.

The present invention is thus a method for predicting the likelihood that a peptide from a protein sequence will be identified by a specific MS based proteomic platform assuming that the protein from which the peptide comes exists in sufficient concentration to be detected by the specific proteomic platform. Thus, yet another object of the present invention is to provide a method that will be useful in all proteomic platforms.

These and other objects are accomplished by the present invention; a method for predicting that a peptide will be detected in a mass spectrometry based proteomic platform. While the method of the present invention is described herein as a series of steps, the sequence of those steps should not be considered as a requirement of the present invention, nor should the claims appended hereto be interpreted in any way as being limited to any particular order of the steps claimed therein. Rather, the sequence of the steps in both this description and the appended claims is merely intended to facilitate an understanding of the invention, and assist in enabling a skilled artisan to make and/or use the invention. Those having ordinary skill in the art will readily recognize that the steps described both in this description and in the appended claims may be performed in an order different than that which is presented, and that performing the steps in an alternative order will accomplish the same end result. Accordingly, the appended claims should in no way be interpreted as limited to the particular order of the steps of the present invention, and this description and the appended claims should be understood as contemplating the performance of the steps of the present invention in any order.

The method of the present invention begins with the step of performing repeated analysis of a sample containing peptides from proteins with known amino acids. Those having ordinary skill in the art will recognize that proteins contain peptides, and peptides are in turn are made up of amino acids, and that the amino acids contained within a great many proteins have been extensively analyzed, and in many cases sequenced, by those having ordinary skill in the art. Accordingly, it should be understood that the term "known" peptides means simply that a portion of the proteins present in the sample have previously been identified, and thus the presence of those peptides in the sample is expected.

The analysis of the sample is preferably performed using at least one mass spectrometer. More than one mass spectrometer may be used, however, the use of several mass spectrometers potentially introduces complications associated with differences between the different machines. If these complications are present, it requires that the practitioner account for these complications when practicing the present invention. Accordingly, while the use of a single mass spectrometer will typically simplify the practice of the present invention, it is not necessarily required.

Those having ordinary skill in the art will recognize that there exist many different types and configurations of mass spectrometers, and it is unnecessary to recite all of these different types and configurations of mass spectrometers to enable a skilled artisan to appreciate their existence. It should therefore be understood that the present invention is capable of being practiced with these different types and configurations of mass spectrometers, and the present invention should in no way be limited to any such type or configuration.

The present invention includes the further step of generating a data set of peptides identified as contained within the sample by the repeated analysis. Peptides included within this data set are limited to the peptides that were identified in at least a portion of the analysis.

The present invention has the further step of calculating the probability that a specific peptide in the data set was detected in the repeated analysis. As used herein, the "probability" that a specific peptide in the data set was detected in the repeated analysis is the ratio of the number of times that the peptide was detected to the number of times the protein that contains the peptide was detected.

The present invention has the further step of creating a plurality of vectors, each vector having a plurality of dimensions, each dimension representing a property of one or more of the amino acids present in each peptide in the data set. Each vector is further associated with the probability that the peptide it describes was detected. The number of dimensions used can vary depending on the specific properties that a user wishes to incorporate in the model.

As used herein, the term "vector" means an ordered collection of n dimensions; such that a vector having n attributes is an ordered collection of n dimensions. For example, a vector constructed to represent a peptide potentially having 20 amino acids could have twenty dimensions, each dimension representing the presence of each of the possible proteogenic amino acids. In this example, the "property" of the amino acid is simply whether it is present or not. However, the "property" of the amino acid should not be limited to the mere presence of the amino acid. "Properties" of amino acids as used herein should be understood to refer to any chemical information, which is both unique and detectable within the particular amino acids, either alone or in combination with the other amino acids in the peptide. Thus, when referring to the "properties", it can be property of an amino acid and/or a property of a peptide and/or a property of a protein. Thus, by way of example and not of limitation, "properties" would include both the position and identity of an amino acid or a portion of the amino acids in the peptide. As a further example "properties" would also include, but not be limited to, hydrophobicity, volume area, pKa, solubility, isoelectric point (pI), Chou-Fasman parameters, hydrogen bonding, protein affinity, gas phase basicity As yet a further example, "properties" would include whether the amino acids contained a phenyl group, or whether the amino acid is aromatic. Regardless of the specific properties selected, the step of creating a plurality of vectors proceeds by assigning each vector a plurality of dimensions, where each dimension represents a property of one or more of the amino acids present in each peptide in the data set. In this manner, a set of vectors is generated which represent a portion of the amino acids present in the data set.

The present invention has the further step of generating an algorithm that is capable of calculating the probability that a given peptide, also represented as a vector, will be detected by a mass spectrometer given that it is present in a sample introduced into the mass spectrometer. The algorithm is generated from both the plurality of vectors and the calculated probabilities that specific peptides in the data set were detected in the repeated analysis. In this manner, the algorithm is able to take as a vector any peptide that might be present in a sample, (hereafter a "hypothetical peptide), and to use that vector to calculate the probability that the hypothetical peptide will be detected by analysis with a mass spectrometer, assuming it is present in the sample.

Preferably, and not meant to be limiting, the algorithm is generated as a data driven model, also known by those having ordinary skill in the art as an empirical model. As the term is used herein, a "data driven model" is any mathematical technique characterized by the use of known data to generate a function that may be applied to similar data to make predictions. In the present invention, the "known data" is the data from the repeated analysis and the calculated probabilities, the "similar data" is the hypothetical peptide expressed as a vector, and the "prediction" is the probability that the hypothetical peptide will be detected by analysis with a mass spectrometer, assuming it is present in the sample. As will be recognized by those having ordinary skill in the art having the benefit of this disclosure, data driven models suitable for use in the present invention include, but are not limited to, multivariate regression, neural networks, support vector machines, and combinations thereof. Accordingly, the present invention preferably utilizes a data driven model to construct an algorithm from the known data from the repeated analysis and the calculated probabilities. The algorithm thus constructed can then analyze any hypothetical peptide to accurately predict whether that peptide will be detected by a mass spectrometry based proteomic platform, assuming that it is present in a sample introduced into the mass spectrometer.

The present invention can be used across the entire spectrum of proteomic platforms. Once the present invention is trained with peptide identifications from a specific proteomic platform, it can accurately predict peptides from a protein sequence that are likely to be identified from the same or very similar proteomic platform. In contrast, if the details of the proteomic platform used in conjunction with the present invention, including but not limited to sample preparations, sample simplifications, the mass spectrometers and the configuration of the mass spectrometers, and the bioinformatic tools are changed, all that is necessary to practice the present invention is to retrain the present invention using data from the proteomic platform as changed.

The steps of the present invention are preferably performed in an automated fashion, and more preferably are performed by a general purpose computer configured to perform the steps. Accordingly, the present invention includes the steps of the present invention recorded in digital form on any media capable of storing an instruction set. By providing that instruction set to a general purpose computer, the general purpose computer is then configured to perform the instructions, and practice the steps of the present invention. As will be recognized by those having skill in the art, the function of any computer programmed by software to perform any series of steps, including the steps of the present invention, can be also be accomplished by configuring computer hardware to perform the identical steps. Further, a computer capable of multiple configurations can be designated as a single purpose computer, dedicated to performing only one task, simply by providing the computer only one software application. Accordingly, the present invention should also be understood to include any computer system, whether multipurpose or single purpose, that has been configured to perform the steps described herein, whether as a series of steps provided to the computer as software, or by configuring the computer's hardware to perform the series of steps described and claimed herein.

BRIEF DESCRIPTION OF THE DRAWINGS

The following detailed description of the embodiments of the invention will be more readily understood when taken in conjunction with the following drawing, wherein:

FIG. 2 are scatter plot diagrams showing the observed vs. predicted peptide probabilities of being proteotypic as found in experiments which demonstrated a preferred embodiment of the present invention.

FIG. 4 are graphs showing the capability of preferred embodiment of the present invention for distinguishing true/false peptide identifications.

DETAILED DESCRIPTION OF THE PREFERRED EMBODIMENTS

Figure 1:
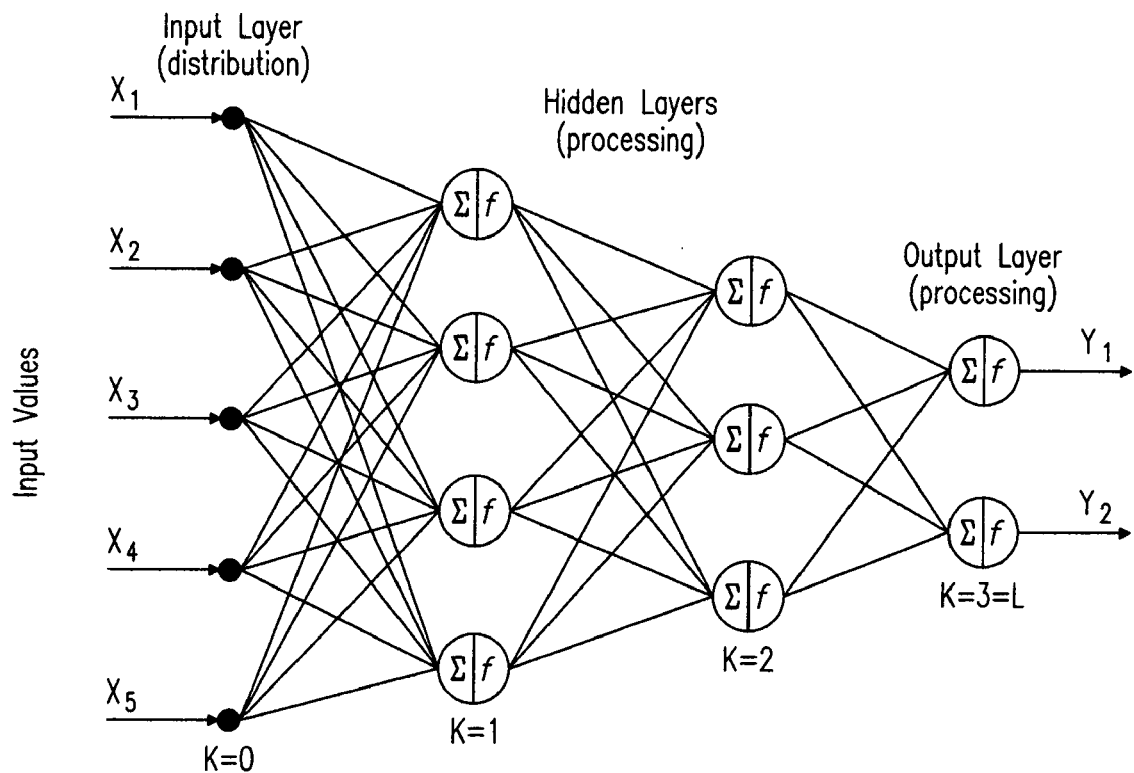
FIG. 1 is a schematic of the data path (from left to right) of a three-layer back propagation neural network used in the experiments which demonstrated a preferred embodiment of the present invention.

For the purposes of promoting an understanding of the principles of the invention, a series of experiments were conducted wherein one embodiment of the invention was demonstrated and reduced to practice.

Peptide identifications from a number of different bacterial organisms and from an array of studies were used to train and test the artificial neural network (ANN). Table 1 lists the bacteria and cites published studies providing the detailed sample preparation for each organism.

TABLE 1

Organisms from which the peptides were identified, number of LC-MS/MS analyses for each organism, number of total spectra, redundant peptides identified from each organism before any filtering and the number of filtered distinct peptides.

| Organism | # of LC-MS/MS | Total spectra | Unfiltered peptides | Filtered peptides |
|---|---|---|---|---|
| D. radiodurans[35] | 1,031 | 491,437 | 56,708 | 21,616 |
| G. mettallireficens | 107 | 400,292 | 54,595 | 21,277 |
| G. sulfurreducens | 791 | 909,730 | 85,358 | 26,446 |
| R. sphaeroides | 1,047 | 432,450 | 57,920 | 22,495 |
| S. tyhpimurium | 492 | 1,692,917 | 116,063 | 32,920 |
| S. oneidensis[36] | 2,315 | 3,040,760 | 117,757 | 33,071 |
| Y. pestis | 719 | 221,196 | 22,322 | 9,898 |
| Total | 6,502 | 7,188,782 | 510,723 | 167,723 |

In general, bacterial cells were cultured in tryptone, glucose, and yeast extract (TGY) medium to an approximate optical density of 600 nm and harvested by centrifugation at 10,000×g at 4° C. Prior to lysis, cells were resuspended and washed 3 times with 100 mM ammonium bicarbonate and 5 mM EDTA (pH 8.4). Cells were lysed by beating with 0.1-mm acid zirconium beads for three, 1-min cycles at 5000 rpm and incubated on ice for 5 min between each cycle. The supernatant containing soluble cytosolic proteins was recovered following centrifugation at 15,000×g for 15 min to remove cell debris. Proteins were denatured and reduced in 50 mM Tris buffer (pH 8.2), 8 M urea, 10 mM tributyl phosphine for 1 h at 37° C. The protein sample was diluted 10 times using 20 mM Tris buffer (pH 8.2) and then digested overnight at 37° C. using sequencing grade, modified porcine trypsin (Promega, Madison, Wis.) at a trypsin:protein ratio of 1:50. The digests were purified using SPE C18 columns (Supelco, Bellefonte, Pa.) according to the manufacturer's instructions and dried under vacuum. Capillary LC systems as described in Shen, Y.; Zhao, R.; Belov, M. E.; Conrads, T. P.; Anderson, G. A.; Tang, K.; Pasa-Tolic, L.; Veenstra, T. D.; Lipton, M. S.; Smith, R. D., "Packed Capillary Reversed- Phase Liquid Chromatography with High-Performance Electrospray Ionization Fourier Transform Ion Cyclotron Resonance Mass Spectrometry for Proteomics" *Anal. Chem.* 2001, 73, 1766-1775. were used for high efficiency reversed phase peptide separations.

Briefly, fused silica capillaries (60 to 80 cm×75 to 150 μm i.d., Polymicro Technologies, Phoenix, Azir.) were packed with 3-μm or 5-μm Jupiter C18 particles (300-Å pore size, Phenomenex, Torrance, Calif.). The sample was directly loaded to the column head using a 6-port switching valve (Valco Instruments, Houston, Tex.). The LC column outlet was connected to a zero dead-volume union (Valco) using PEEK tubing (380 μm i.d., Upchurch Scientific, Oak Harbor, Wash.) to position a steel screen having 2 μm pores (Valco). The union's other end was connected to a 3-cm length of fused silica capillary tubing (50 μm i.d.×200 μm o.d., Polymicro Technologies) tapered to form an ESI emitter. The LC gradient separation was conducted in constant pressure mode (5,000 to 10,000 psi) by replacing mobile phase A [$H_2O$/acetic acid/trifluoroacetic acid (TFA), 100:0.2:0.05, v/v, Aldrich, Milwaukee, Wis.] with mobile phase B (acetonitrile/$H_2O$/TFA, 90:10:0.1, v/v) in a stainless steel static mixer (2.5 mL). Two ISCO pumps (Model 100 DM, ISCO) were used for delivery of the mobile phases.

Conventional 3-D ion trap mass spectrometers (Finnigan model LCQ XP, ThermoQuest Corp., San Jose, Calif.) were used for the ESI-MS/MS measurements. The distance between the ESI emitter tip and the MS inlet capillary was ~1 mm, and the heated capillary temperature and ESI voltage (applied on the column outlet connection union) were set at 200° C. and 2 kV, respectively. The three most abundant ions from MS analysis were selected at the m/z range of 400-2000. A collision energy setting of either 35% or 45% was applied for ion fragmentation and a data-dependent analysis mode was applied to discriminate against previously analyzed ions.

The software SEQUEST (ThermoQuest Corp.) was used for identification of peptides from the LC-MS/MS analyses. The mass tolerance of ±3 Da was used for database searching without considerations of peptide modifications. A ΔCn value of >0.1 was used to filter the spectra, and threshold values for XCorr were as follows: XCorr>1.6 for +1 charged fully tryptic (mass<1000 Da), XCorr>2.2 for +1 charged fully tryptic (mass>1000 Da), and XCorr>2.8 for +1 charged partially tryptic (mass>1000 Da) peptides; XCorr>2.2 for +2 charged fully tryptic, XCorr>3 for +2 charged partially tryptic peptides; XCorr>2.9 for +3 charged fully tryptic, XCorr>3.7 for +3 charged partially tryptic peptides. Only peptides having 5 to 50 amino acid residues were considered.

As described in Werbos, P. J., *The Roots of Backpropagation*. John Wiley & Sons: New York, 1994, Werbos, P. J. New tools for predictive and analysis in the behavioral sciences (Ph.D. Thesis, Harvard University). Ph.D., Harvard University, Cambridge, Mass., 1974, and Baczek, T.; Wiczling, P.; Marszall, M.; Heyden, Y. V.; Kaliszan, R., Prediction of peptide retention at different HPLC conditions from multiple linear regression models. *J. Proteome Res.* 2005, 4, 555-563, an artificial neural network (ANN) is an information processing paradigm that learns by example rather than by following instructions. It is composed of a set of highly interconnected neurons or nodes and these neurons work in parallel to solve a complex problem. The experiments described herein used a back-propagation neural network (BPN), a supervised feed-forward network. Its architecture consisted of one input layer, zero or more hidden layers, and one output layer, as shown in FIG. 1. Each layer contains nodes, and the nodes in each layer are fully or partially connected to the nearest layers above or below. The nodes in the input layer receive the input vectors and distribute the input data values to the next hidden layer through weighted connections; the nodes in the output layer produce the desired resultant output. Nodes in the hidden layer performed two calculations including summing the products of connection weights and the signals from the previous layer using equation (1) and calculating their output using a sigmoid function (2).

$$Net_j = \sum_{i=1}^{n} w_{ij} O_i \quad (1)$$

$$O_j = 1/(1+e^{-Net_j}) \quad (2)$$

where the $Net_j$ represents the net input signal to the j node, i represents the nodes in the previous layer, $w_{ij}$ is the weight value associated with the connection from node i to node j, value n represents the number of nodes in the previous layer connected to the node j, and $O_i$ is the output signal from the node i. The node in the output layer also applied these two calculations to produce its output.

The output-layer error was calculated by subtracting the actual output from the target output during the training of the network; the network passed the output-layer error to the hidden layer, while the nodes in the hidden layer adjusted the weights to reduce their errors. The process of changing weight values so that the actual output become closer to the target output was performed iteratively many times using the training data in the training phase. This backpropagation of error algorithm is only one of many that can be used.

This work used ANN software NeuroWindows Version 4.5 (Ward Systems Group, USA), with a standard back propagation algorithm running on a Pentium 3.0 GHz personal computer. The network model was trained with a learning rate and momentum term of 0.1 and 0.9 respectively. The models were tested at training epoch numbers from 10 to 100 and the best performance was obtained at about 70 epochs after which the performance deteriorated.

There are several ways for peptides to be incorporated (encoded) in a statistical prediction algorithm. One of the simplest ways is to encode the amino acid composition of the peptides, tracking how many times each amino acid residue is found in each peptide. One of the most computationally complex ways is by fully describing the peptide sequence, i.e. identifying what amino acid is occupying which position in each peptide. In general, the larger the training set the more complex the encoding can be without over-fitting the data.

In this study, two peptide encoding schemes were examined for input to the neural network: fully and partially encoded peptide sequences. The fully encoded peptide sequence model described the exact amino acid residue in each position of the peptide sequence (up to 50 residues). The partially encoded peptide sequence model described the exact amino acid residues for the 3 amino acids at the N-terminus and the 3 amino acids at the C-terminus of the peptide. The remaining amino acid residues are represented by a single vector.

Thus, in the fully encoded peptide sequence model used in these experiments, each vector was composed of 21 dimensions and each dimension represented an individual amino acid residue. All the vectors representing the exact position of an amino acid residue in the peptide contain 20 zero values and one numerical value representing the amino acid residue. In contrast, the vector in the partially encoded peptide sequence model that is used to describe the amino acid composition of the remainder of the peptide sequence often has more than one non-zero value.

Eight parameters related to peptide structure/sequence were also investigated. These parameters were the 3 amino acid residues proceeding and following the modeled peptide, the hydrophobicity values of proceeding and following neighboring amino acid sequences, the peptide cleavage at each end, and the peptide LC normalized elution time (NET) value. 279 input nodes were necessary to describe the partially encoded peptide sequence network model while 1182 input nodes were used to describe the fully encoded peptide sequence network model. All input vectors were normalized to a range of 0-1 using the following normalization function:

$$x_{nor} = \frac{x\text{-min}}{\text{max-min}}$$

where max and min are the maximum and minimum values, respectively, for each input variable.

For the fully encoded peptide sequence model, the position of each amino acid residue is preferably identified. Since peptides with up to 50 amino acid residues were considered in these experiments, 1050 input nodes were used to represent each of the peptides (50×21). For the partially encoded peptide sequence the 3 N-terminal amino acids are represented by 63 input nodes (3×21). Another 63 nodes were used to describe the 3 C-terminus amino acid residues. Finally, another 21 nodes were used to represent the amino acid composition for the remaining residues in the peptide.

Several aspects of the encoding were common for both models. The three amino acids preceding the peptide of interest were represented by 63 nodes (3×21). The three amino acids following the peptide of interest were represented by another 63 nodes. The hydrophobicity value (calculated by averaging the hydrophobicity of all the different amino acid residues to one value) of the preceding neighboring amino acid residue sequence was represented by 1 input. Another input was used for the hydrophobicity value of the following neighboring amino acid residues. Two input nodes were used for the likelihood of the peptide cleavage at the beginning and the end of the peptide of interest. The product of cleavage probabilities at both ends was described by one input node defined by the following equation, $$\text{Cleavage likelihood at amino acid position} = \left|\frac{x_2 - x_1}{y}\right|$$

where $x_1$ is the number of times that the amino acid previous to the first amino acid of the examined peptide was detected; $x_2$ is the number of times that the first amino acid (C-terminus) of the examined peptide examined amino acid was detected and y is the total number of different LC-MS/MS experiments the corresponding protein (i.e. the protein which the peptide came from) was identified.

Finally the liquid chromatography (LC) normalized elution time (NET) value of the peptide of interest was represented by one node.

For each peptide in the training set, a value was assigned that described if that peptide was or was not identified. This number was calculated using the following equation, which is defined as the observed likelihood of a peptide being proteotypic:

$$\text{Peptide observed likelihood of being proteotypic} = \frac{x}{y}$$

where x is the number of different LC-MS/MS experiments in which a peptide was identified and y is the total number of LC-MS/MS experiments in which the corresponding protein (i.e. the protein which the peptide came from) was identified. If the peptide was identified several times in the same LC-MS/MS experiment (e.g., due to selection of different charge states or broad chromatographic peaks) it was only counted once in that experiment. This equation illustrates that a peptide can have an observed likelihood of being proteotypic with a range from 0 to 1, where 0 indicates that the peptide was never identified while 1 indicates that the peptide was identified the same number of times as its respective protein (i.e. x=y).

In this study data from 7 different microorganisms were used to train and test the model. As these are "real-world" proteomic data, the exact amount of each protein was not known, making it impossible to normalize the number of peptides identified from each protein to the respective protein concentration. In other words, if only a few peptides where identified from a protein, it is not known if this is because the protein was present in low abundance or if most of its peptides are not proteotypic. To avoid this problem we chose to utilize only peptides from highly abundant proteins, thus assuring that when peptides are not detected, it is because they are not proteotypic. Thus, only peptides coming from proteins that had been identified by ≧7 unique peptides in the same or different LC-MS/MS analyses were considered for the training/testing of the model. Among the 167,723 peptides that passed the SEQUEST score thresholds shown in Table 1 only 71,079 came from proteins identified ≧7 times. For each peptide identified from a protein, another peptide that had not been identified was selected from the same protein. Although the unidentified peptide was randomly selected, it was required to have the same tryptic state and zero sequence overlap with the observed peptide. The addition of unobserved peptides allows the training of the model to provide better predictive capability and resistance to interference. Lastly, 98% (139,986) of the peptides passing the score thresholds were randomly selected as the training dataset while 2% (2,172) of the peptides were randomly selected as the testing dataset. Although the peptides were randomly selected, the ratio of observed to unobserved peptides was maintained at 1:1 in both the training and testing dataset.

While the experiments described herein did not take into account protein size or protein concentration, the present invention should be considered as having contemplated these parameters, as these are known to be important factors in determining how many peptides are going to be identified from a specific protein. For examples for two proteins of the same concentration but different size (i.e. MW or length), it is more likely that a mass spectrometer will detect more peptides from the larger protein. Furthermore, more peptides are going to be identified from a protein if it exists in higher concentration in the sample. The present invention would model both these parameters simply by encoding, for example, the number of in silico peptides of each protein. In this example it would be preferred to count only peptides with a MW>400 as this is the practical low mass to charge ratio the mass spectrometers are tuned to search for peptides.

Protein size could also be taken in to account in the selection of peptides that are included in the training set. In the experiments described herein, peptides were selected that came from proteins that had been identified by at least 7 unique peptides in the same or different LC-MS/MS experiments. By way of example, and not limitation, this number could be increased for larger proteins and decreased for smaller proteins. Furthermore, the absolute or relative concentration of a protein could also be taken into account in the present invention.

One possibility would be by performing an absolute or relative quantitation of the proteins of the samples that are to be used for the training of the model. Another possibility would be by introducing the ratio of the number of times the protein has been identified to the number of the LC-MS/MS analyses. High abundant proteins will have higher ratios than lower abundant proteins. This way is probably preferred, as it does not require any previous quantitation of the sample and could even performed with the current data. Another possibility would be encoding a ratio that would take into account both size and concentration of the protein. For example, and not meant to be limiting, the ratio X/Y×Z could be encoded where X=number of different experiments a protein has been identified, Y=total number of LC-MS/MS experiments that the specific protein can be present, and Z is the size of the protein. The size of the protein can be expressed in different ways. For example, but not meant to be limiting, the size of the protein can be expressed as a) MW of the protein, b) number of amino acid residues, c) number of in silico peptides with a MW>400. The number of the in silico peptides will change as a function of the protein digestion method and the number of missed cleavages that will need to be considered. Expressing the size of the protein as a number of in silico peptides is preferred, as it takes into account the way the protein has been digested while the other methods are constant and as a result non-sensitive to the digestion method. This ratio thus provides a relative idea of the concentration of the protein at the same time that it normalizes for the size of the protein.

Several peptide related parameters were considered as inputs to the artificial neural network. The first parameter considered was the predicted retention time of the peptide, which is partially dependent on peptide hydrophobicity. Le Bihan et al. (discussed above) explained that it is better to use the predicted retention time rather than calculated hydrophobicities derived from published hydrophobic scales as each different application require a unique/specific scale. In addition, the retention time predictor works as a quick filter by excluding extremely hydrophilic peptides (i.e. predicted normalized elution time <0) and extremely hydrophobic peptides (i.e. predicted normalized elution time >1) from being selected as proteotypic. Furthermore, as described in Petritis, K.; Kangas, L. J.; Ferguson, P. L.; Anderson, G. A.; Pasa-Tolic, L.; Lipton, M. S.; Auberry, K. J.; Strittmatter, E. F.; Shen, Y.; Zhao, R.; Smith, R. D., Use of artificial neural networks for the accurate prediction of peptide liquid chromatography elution times in proteome analyses. *Anal Chem* 2003, 75, (5), 1039-48 and Petritis, K.; Kangas, L. J.; Yan, B.; Strittmatter, E. F.; Monroe, M.; Qian, W.-J.; Adkins, J. N.; Moore, R. J.; Xu, Y.; Lipton, M. S.; II, D. G. C.; Smith, R. D., Improved peptide elution time prediction for reversed-phase liquid chromatography-MS by incorporating peptide sequence information. *Anal Chem* 2006, submitted, the models available for use in retention time prediction are far more accurate than previously published models and are therefore superior to calculated hydrophobicities.

Figure 2A:
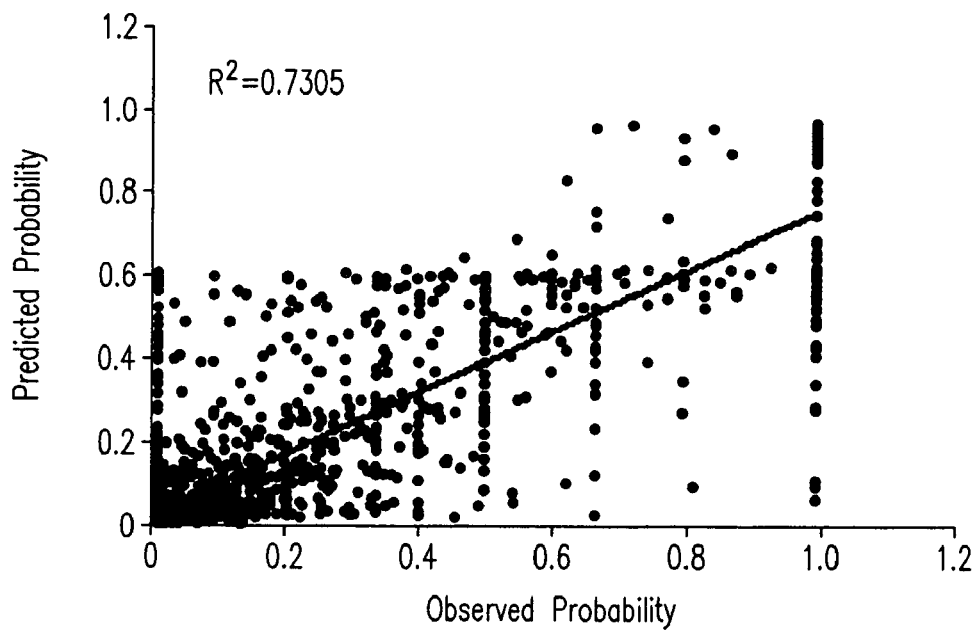
FIG. 2(A) shows the results for a partially encoded peptide sequence model with 279 input nodes, 5 hidden nodes and 1 output node.
Figure 2B:
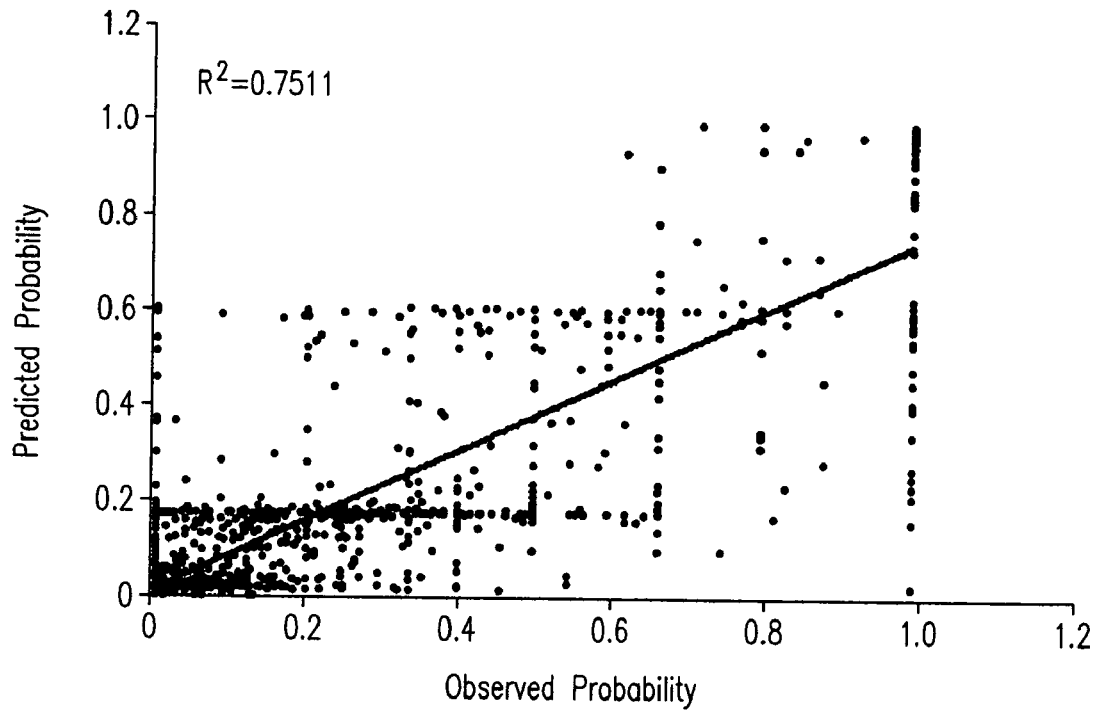
FIG. 2(B) shows the results for a fully encoded peptide sequence model with 1182 input nodes, 5 hidden nodes and 1 output node.

The second parameter considered was the composition and order of the peptide amino acid sequence. By incorporating the peptide sequence, the model can differentiate between fully and partially tryptic peptides. This is important information for the model as fully tryptic peptides have inherently higher likelihood to be detected as the proteins are digested with trypsin. Furthermore, valuable information such as neighboring amino acids residues that can accept a proton in the gas phase is also available to the model. Two different models were evaluated: one that encoded the full peptide sequence and another that only encoded the 3 N-terminal amino acids and the 3 C-terminal amino acids while tracking the overall amino acid composition of the remainder of the peptide. This is a much more simplistic model (i.e. 279 vs. 1182 nodes) and should work better when there is a limited amount of training data available. FIGS. 2A and 2B compare the two models. For the same amount of hidden nodes (i.e. 5) the fully encoded peptide sequence model outperforms the partially encoded one. Indeed, the fully encoded model achieves a mean square error (MSE) and R-square of 0.069 and 0.75 which are each better than the partially encoded model (MSE of 0.072, $R^2$ of 0.73).

Furthermore, several parameters that might prevent trypsin from cleaving a peptide were considered. These were the information about the 3 amino acid residues preceding and following the peptide of interest, as well as the average hydrophobicity of several amino acid residues preceding and following the peptide of interest. For the latter, the average hydrophocity of 10, 15 and 20 residues was investigated, and 15 residues were found to provide the best results as shown in table 2.

TABLE 2

Examination of hydrophobicity contributions from various length of nearest-neighbor peptides.

| Length of neighbor peptide | R-Square | MSE |
|---|---|---|
| 10 | 0.84 | 0.043 |
| 15 | 0.86 | 0.038 |
| 20 | 0.85 | 0.040 |

Finally, the cleavage likelihood at each amino acid position, defined by the following equation, was incorporated into the network $$\text{Cleavage likelihood at amino acid position} = \left| \frac{x_2 - x_1}{y} \right|$$

where $x_1$ is the number of times that the amino acid previous to the first amino acid of the examined peptide was detected; $x_2$ is the number of times that the first amino acid (C-terminus) of the examined peptide examined amino acid was detected and y is the total number of different LC-MS/MS experiments the corresponding protein (i.e. the protein which the peptide came from) was identified.

Figure 2C:
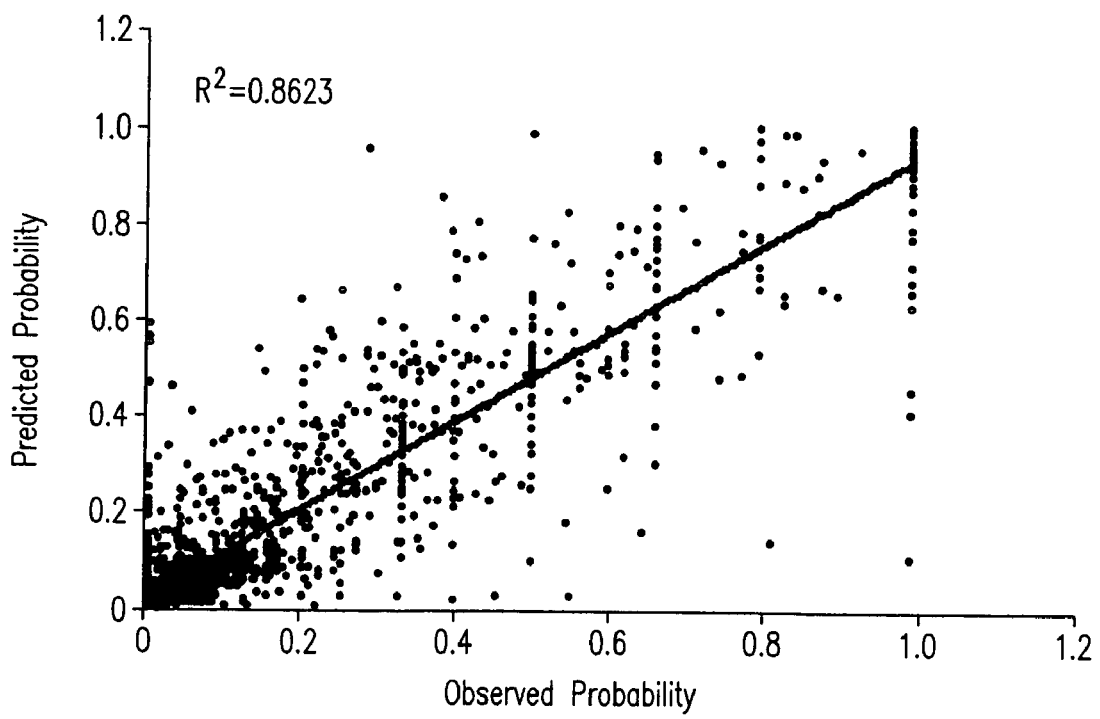
FIG. 2(C) shows the results for a peptide sequence model with configuration of 1182 input nodes, 18 hidden nodes and 1 output node.

Finally, different numbers of hidden nodes were evaluated (5, 10, 15, 18, and 20) with 18 hidden nodes being found as the optimum number as shown in Table 3 and FIG. 2C.

TABLE 3

The influence of hidden node number on the ANN prediction accuracy.

| Hidden nodes | R-Square | MSE |
|---|---|---|
| 5 | 0.75 | 0.069 |
| 10 | 0.78 | 0.050 |
| 15 | 0.83 | 0.046 |
| 18 | 0.84 | 0.043 |
| 20 | 0.83 | 0.050 |

The optimum model provided a MSE of 0.037 and $R^2$ of 0.86 (FIG. 2C). The addition of the peptide hydrophobicity calculated by different hydrophobic scales as shown in Eisenberg, D.; Schwarz, E.; Komaromy, M.; Wall, R., Analysis of Membrane and Surface Protein Sequences with the Hydrophobic Moment Plot. *Journal of Molecular Biology* 1984, 179, (1), 125-142, and Charton, M.; Charton, B. I., The Structural Dependence of Amino-Acid Hydrophobicity Parameters. *Journal of Theoretical Biology* 1982, 99, (4), 629-644 did not improve the model.

Figure 3:
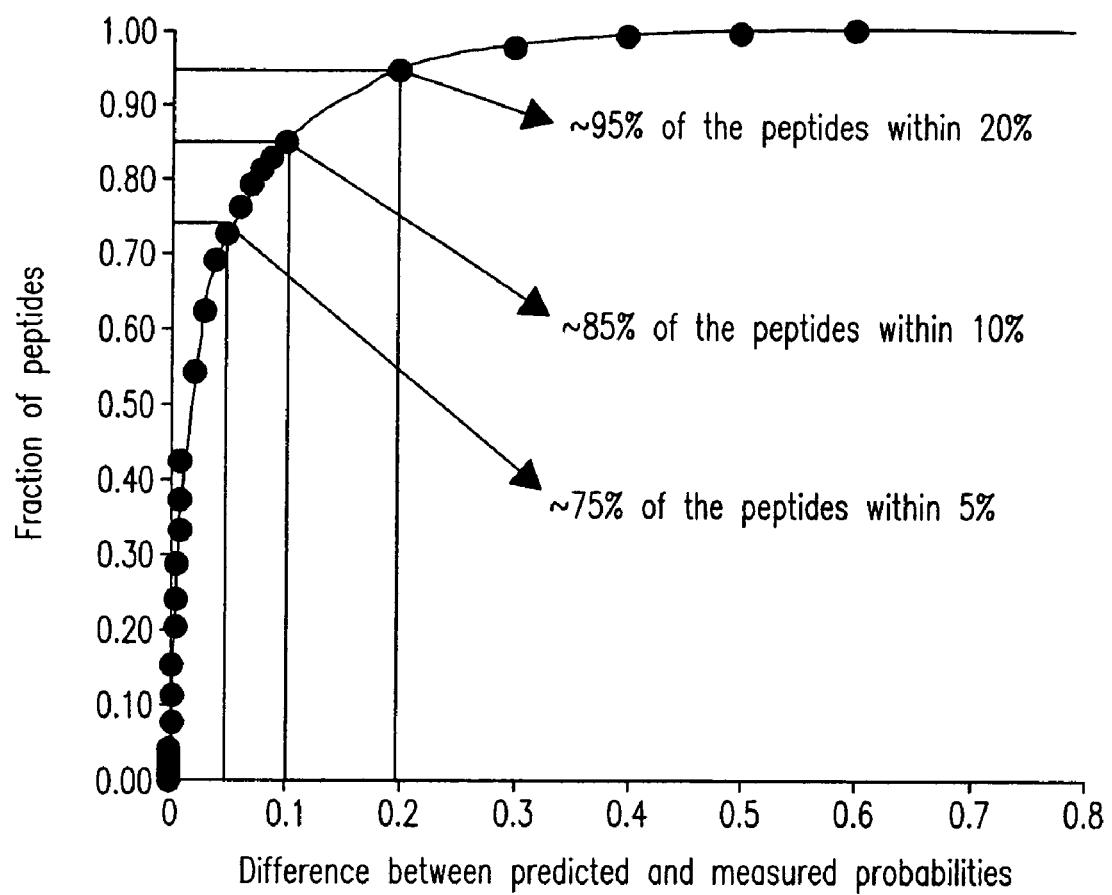
FIG. 3 is a cumulative density function graph showing the accuracy of preferred embodiment of the present invention for prediction of proteotypic peptides as demonstrated by the experiments described herein. As shown in the graph, the likelihood differences between the predicted and observed probabilities were <±20% for ~95% of the tested peptides, <±10% for ~85% of the tested peptides, and <±5% for ~75% of the tested peptides.

As shown in FIG. 3, the model accuracy for predicting proteotypic peptides is high with 85% of the tested peptides having a deviation of <±10% between the observed and predicted likelihood of a peptide being proteotypic while about 75% of the tested peptides deviated <±5% between the observed and predicted values. Most of the model's prediction capability comes from the incorporation of the fully encoded peptide sequence in the model, while the rest of the parameters have relatively minor contributions to the model's accuracy.

Figure 4A:
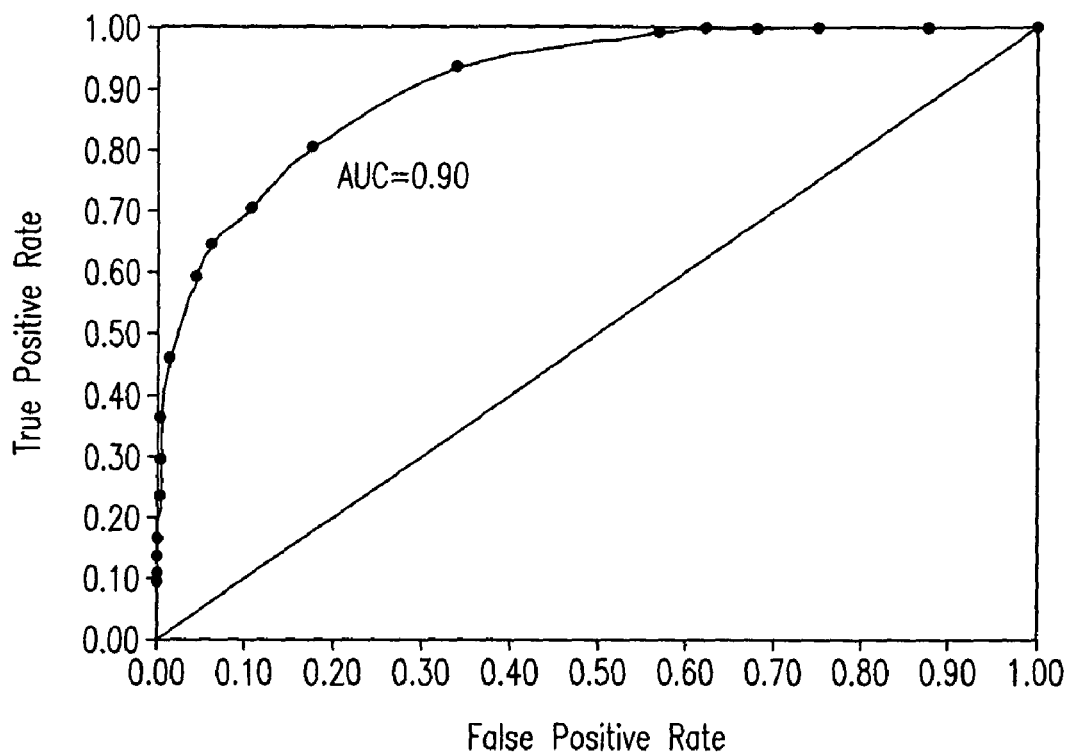
FIG. 4(A) is the ROC curve and FIG. 4(B) is the proteotypic peptide true/false rates at various detection probabilities predicted from the ANN model obtained in this study.
Figure 4B:
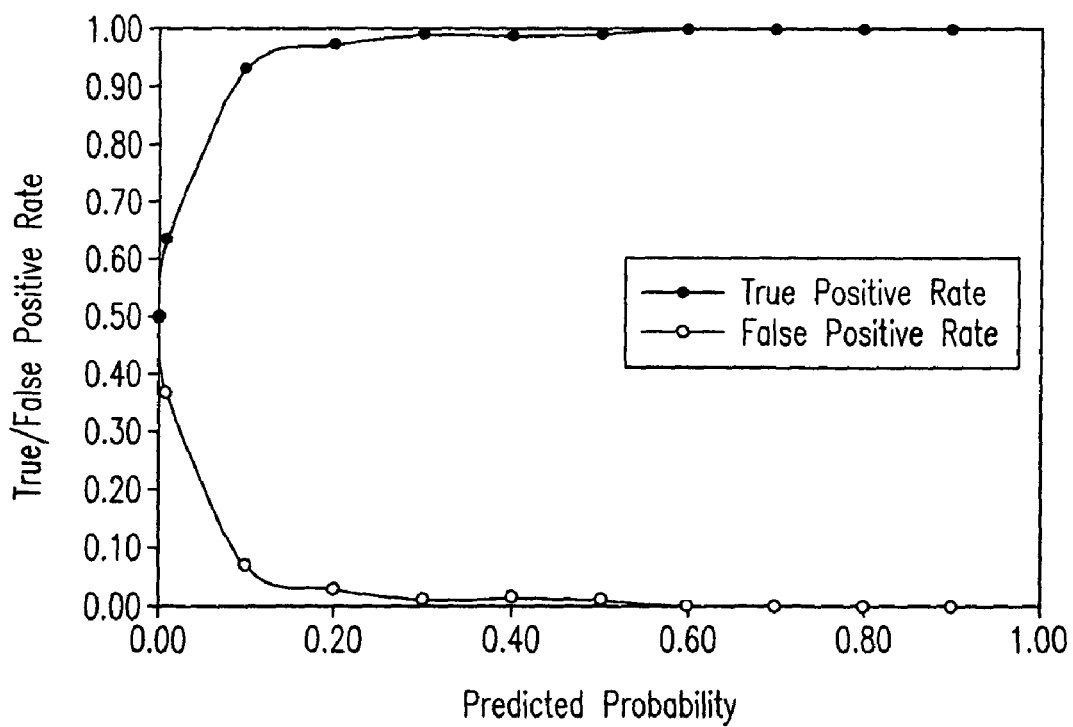

FIG. 4 illustrates the peptide identification true/false positive rates obtained from the ANN predictor for the testing dataset. The area under the receiver operating characteristics (ROC) curve (FIG. 4A) of 0.90 (close to the ideal value of 1.0) demonstrates that there is a 90% likelihood for the peptide to be correctly assigned as being proteotypic. The true/false positive rates at various threshold values of the ANN prediction probabilities in FIG. 4B show that peptides with a score >0.3 are those that are very likely correctly identified in LC-MS/MS analyses (i.e., a >99% true positive rate). Peptides having a score <0.1 are likely to be false positives, as shown in see FIG. 4B. The present predictor was thus shown to provide an additional level of confidence for peptide identifications when used in conjunction with other parameters such as SEQUEST XCorr or a discriminant function as described in Strittmatter, E. F.; Kangas, L. J.; Petritis, K.; Mottaz, H. M.; Anderson, G. A.; Shen, Y.; Jacobs, J. M.; Camp, D. G., 2nd; Smith, R. D., Application of peptide LC retention time information in a discriminant function for peptide identification by tandem mass spectrometry. *J Proteome Res* 2004, 3, (4), 760-9.

While the invention has been described in connection with the specific embodiments described herein, those having ordinary skill in the art will recognize that the present invention should in no way be limited to the specific details of the embodiment used in these experiments.

The invention claimed is:

1. A method for predicting that a peptide will be detected in a mass spectrometry based proteomic platform comprising the steps of:
    a. using at least one mass spectrometer, performing repeated analysis of a sample containing peptides from proteins with a known amino acid sequence,
    b. generating a data set of peptides identified as contained within the sample by the repeated analysis,
    c. calculating the probability that a specific peptide in the data set was detected in the repeated analysis,
    d. creating a plurality of vectors, each vector having a plurality of dimensions, each dimension representing a property of one or more of the amino acids present in each peptide in the data set,
    e. generating an algorithm from the plurality of vectors and the calculated probabilities that specific peptides in the data set were detected in the repeated analysis, said algorithm capable of calculating the probability that a hypothetical peptide represented as a vector will be detected by a mass spectrometry based proteomic platform, given that the corresponding peptide is present in a sample introduced into a mass spectrometer.

2. The method of claim 1 wherein the step of generating an algorithm from the data set is by a data driven model.

3. The method of claim 2 wherein the data driven model is selected from the group: multivariate regression, neural network, support vector machine, and combinations thereof.

4. An apparatus for predicting that a peptide will be detected in a mass spectrometry based proteomic platform comprising:
    a computer configured to:
        i. accept data from repeated mass spectrometric analysis of a sample containing peptides from proteins with a known amino acid sequence,
        ii. accept a data set of peptides identified as contained within the sample by the repeated analysis,
        iii. calculate the probability that a specific peptide in the data set was detected in the repeated analysis,
        iv. create a plurality of vectors, each vector having a plurality of dimensions, each dimension representing a property of one or more of the amino acids present in each peptide in the data set,
        v. generate an algorithm from the plurality of vectors and the calculated probabilities that specific peptides in the data set were detected in the repeated analysis, said algorithm capable of calculating the probability that a hypothetical peptide represented as a vector will be detected by a mass spectrometry based proteomic platform given that the corresponding peptide is present in a sample introduced into a mass spectrometer.

5. The apparatus of claim 4 wherein the algorithm generated from the data set is generated by a data driven model.

6. The apparatus of claim 5 wherein the data driven model is selected from the group: multivariate regression, neural network, support vector machine, and combinations thereof.

* * * * *

UNITED STATES PATENT AND TRADEMARK OFFICE
CERTIFICATE OF CORRECTION

PATENT NO. : 7,756,646 B2  Page 1 of 1
APPLICATION NO. : 11/394839
DATED : July 13, 2010
INVENTOR(S) : Lars Kangas, Richard D. Smith and Konstantinos Petritis It is certified that error appears in the above-identified patent and that said Letters Patent is hereby corrected as shown below:

col. 9 line 7   Phoenix Azir. --

Should be replaced to read

-- Phoenix, AZ --

Signed and Sealed this

Thirtieth Day of November, 2010

David J. Kappos
*Director of the United States Patent and Trademark Office*